United States Patent [19]

Hüttenrauch et al.

[11] Patent Number: 4,672,652
[45] Date of Patent: Jun. 9, 1987

[54] RADIODIAGNOSTIC APPARATUS WITH SEMITRANSPARENT DIAPHRAGM

[75] Inventors: Gerd Hüttenrauch, Uttenreuth; Wolfango Jann, Buckenhof; Feliks Kranvogel, Neunkirchen, all of Fed. Rep. of Germany

[73] Assignee: Simens Aktiengesellschaft, Berlin and Munich, Fed. Rep. of Germany

[21] Appl. No.: 815,702

[22] Filed: Jan. 2, 1986

[30] Foreign Application Priority Data

Jan. 11, 1985 [DE] Fed. Rep. of Germany ....... 3500812

[51] Int. Cl.⁴ .............................................. G21K 1/04
[52] U.S. Cl. ................................... 378/152; 378/150; 378/151; 378/148
[58] Field of Search ............................ 378/156–158, 378/150–153, 145–148, 99, 205; 358/111

[56] References Cited

U.S. PATENT DOCUMENTS

| | | | |
|---|---|---|---|
| 2,943,205 | 6/1960 | Kazan et al. | 250/206 |
| 3,402,292 | 9/1968 | Baecklund | 378/157 |
| 3,631,249 | 12/1971 | Friede et al. | 378/157 |
| 3,755,672 | 8/1973 | Edholm et al. | 378/158 |
| 3,912,936 | 11/1975 | Cunninghame et al. | 250/512 |
| 4,101,961 | 7/1978 | Reiber | 358/111 |

FOREIGN PATENT DOCUMENTS

| | | |
|---|---|---|
| 0083465 | 12/1982 | European Pat. Off. . |
| 1800879 | 5/1970 | Fed. Rep. of Germany . |
| 2053089 | 5/1972 | Fed. Rep. of Germany . |
| 2345406 | 7/1975 | Fed. Rep. of Germany ...... 378/150 |
| 2905202 | 8/1980 | Fed. Rep. of Germany . |
| 3030332 | 2/1982 | Fed. Rep. of Germany ...... 378/147 |
| 2429584 | 2/1980 | France .............................. 378/156 |

Primary Examiner—Craig E. Church
Assistant Examiner—John C. Freeman
Attorney, Agent, or Firm—Mark H. Jay

[57] ABSTRACT

The invention relates to a radiodiagnostic apparatus with an x-ray tube, a diaphragm which is semitransparent at least areawise and which clears a slit variable in its width and letting the radiation go through, with an x-ray image intensifier and a television camera coupled thereto for the generation of video signals which is connected to a monitor for reproduction of the video signals. The diaphragm consists of several individual blades which abut against one another in parallel on both sides of the slit and are adjustable in longitudinal direction individually dependent on the size of the object to be viewed. To the television camera an evaluating circuit is connected which supplies a control signal obtained from the video signal to a setting device for the individual blades.

7 Claims, 3 Drawing Figures

RADIODIAGNOSTIC APPARATUS WITH SEMITRANSPARENT DIAPHRAGM

BACKGROUND OF THE INVENTION

The invention relates to a radiodiagnostic apparatus with an X-ray tube, a diaphragm which is semitransparent in at least one region and which clears a slit of variable width to let radiation pass, with an x-ray image intensifier and a television camera coupled thereto for the generation of video signals, the camera being connected with a monitor for the reproduction of the video signals.

German Offenlegungsschrift No. 1,800,879 discloses a primary ray diaphragm for x-ray examination apparatus. Here, a semitransparent diaphragm consisting of two diaphragm plates attenuates the lateral radiations in the x-ray beam. Otherwise, particularly in the case of extremities, the unattenuated beam would directly strike the x-ray image intensifier input screen. This would produce bright areas which impair the perception of details in the actual viewing area. By the use of the semitransparent diaphragm plates these overradiated (or "bloomed") lateral areas are attenuated, so that the visibility in the area of interest is increased, although high-contrast objects (for example, surgical instruments brought in from the side) are still clearly visible. To properly orient the test object with respect to the radiodiagnostic apparatus, the diaphragm plates are rotatable on a diaphragm disk. For manual adjustment of the width of the non-attenuated ray path, the two diaphragm plates can be moved toward each other, until (in the ideal case) overradiated areas have disappeared. In the normal case of non-rectilinear contours, contour adaptation cannot be achieved with the rectilinear end faces of the diaphragm plates. Either a large portion of the object to be examined is attenuated as well, or else large parts of the television picture are still overradiated, so that the visibility of details continues to be reduced.

From German Offenlegungsschrift No. 29 05 202 a viewer ("light viewing box") is further known, where for the observation of transparent, rectangular pictures the image support can be darkened by a plurality of parallel and narrow cover strips. By placing pictures on the edge of the viewer, their size is picked up automatically. Subsequently only those strips which cover the picture are moved by a motor until the film is exposed also at its lower edge. Several films can be exposed simultaneously only if they are of the same vertical size. Adaptation to irregular contours is impossible by using the blades of this viewer.

One object of the invention is to provide, for a radiodiagnostic apparatus of the initially mentioned kind, a semi-transparent diaphragm which adapts itself as exactly as possible to the contours of the object to be examined, so that only small areas of the object being examined, or none at all, are covered up, or only small areas in the vicinity of the object are uncovered.

SUMMARY OF THE INVENTION

According to the invention, the diaphragm comprises a plurality of individual blades, which abut and are parallel to each other. The blades are arranged into two opposed groups which are on both sides of the slit and are individually longitudinally slidable dependent on the size of the object to be viewed. There is connected to the television camera an evaluating circuit which supplies a control signal obtained from the video signal to a setting device for the individual blades. The blades of the diaphragm are automatically moved toward each other until each individual blade reaches the outer contours of the object being examined.

Advantageously the longitudinal direction of the blades is perpendicular to the center line of the slit. A better adaptation of the blades to the contour of the object being examined can be obtained when the longitudinal direction of the blades makes an angle of between 20° and 90° with the center line of the slit. It has been found to be advantageous when the angle between the longitudinal direction of the blades and the center line of the slit is 45°. A simple control of the blades results when each individual blade is displaced by a corresponding motor. The mechanical construction can be simplified when there are provided for each side of the diaphragm, i.e. each group of blades, a motor which drives a roller, and at least one coupling magnet, the motor and magnet being controlled by the evaluating circuit, and when the blades can be coupled with the roller by the coupling magnet. Reliable adjusting of the blades is achieved when at least one part of each of the blades is designed as a toothed rack and when the roller is designed as a toothed roller. The mechanical cost can be further reduced when a coupling magnet is provided which is displaced mechanically and couples the blades individually with the roller. Parallel actuation of the blades can be achieved when a coupling magnet is associated with each blade, the coupling magnet being individually actuated by the evaluating circuit. The evaluating circuit is further simplified when the coupling magnets are actuated individually, one after the other. Rapid adjusting of the blades can be achieved when the coupling magnets are actuated by the evaluating circuit alternately in multiplexing. The electronic engineering can be simplified when, in radio diagnostic apparatus in which the diaphragm is arranged on a rotatable diaphragm ring, the television camera and the diaphragm are coupled in their rotation in such a way that the longitudinal direction of the blades always lies in the direction of the television's horizontal scan.

Advantageously, the evaluating circuit comprises a circuit for position determination of the blades within the video picture. To the circuit are supplied the clock pulses of the television camera and control signals, which identify the particular blade being actuated. The video signal is supplied to an adaptation stage, and the adaptation stage and the circuit are connected with a gate circuit to which a peak value detector is connected. The output signal of the detector is supplied to a comparator stage which compares the output signal with an adjustable threshold value, and the comparator stage controls the coupling magnets. Optimum control of the blades is achieved if the threshold value is selectable to correspond to the transmission characteristics of the organ under investigation.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
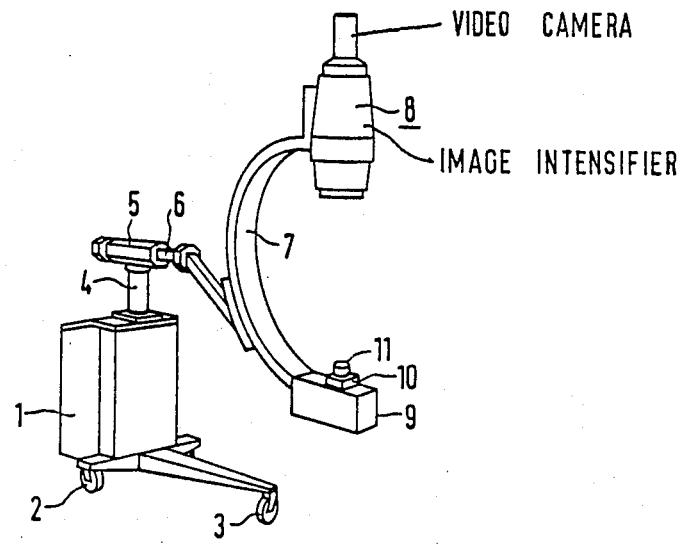
FIG. 1 shows a radiodiagnostic apparatus of the type in which the invention is installed.

In FIG. 1 is shown a wheelable radiodiagnostic apparatus 1 with wheels 2 and 3, such as is frequently used in surgery. It comprises a vertical support 4 adjustable in height with a sleeve 5 in which a horizontal support 6 is slidably mounted. At the end of the horizontal support 6 a C-arch 7 is slidably arranged. At one end of C-arch 7 which is located the housing 8 for an x-ray image intensifier and a television camera, and at the other end the x-ray tube housing 9. At the x-ray tube housing 9 a primary ray shield 10 is arranged, to which a tube (barrel) 11 is fastened.

Figure 2:
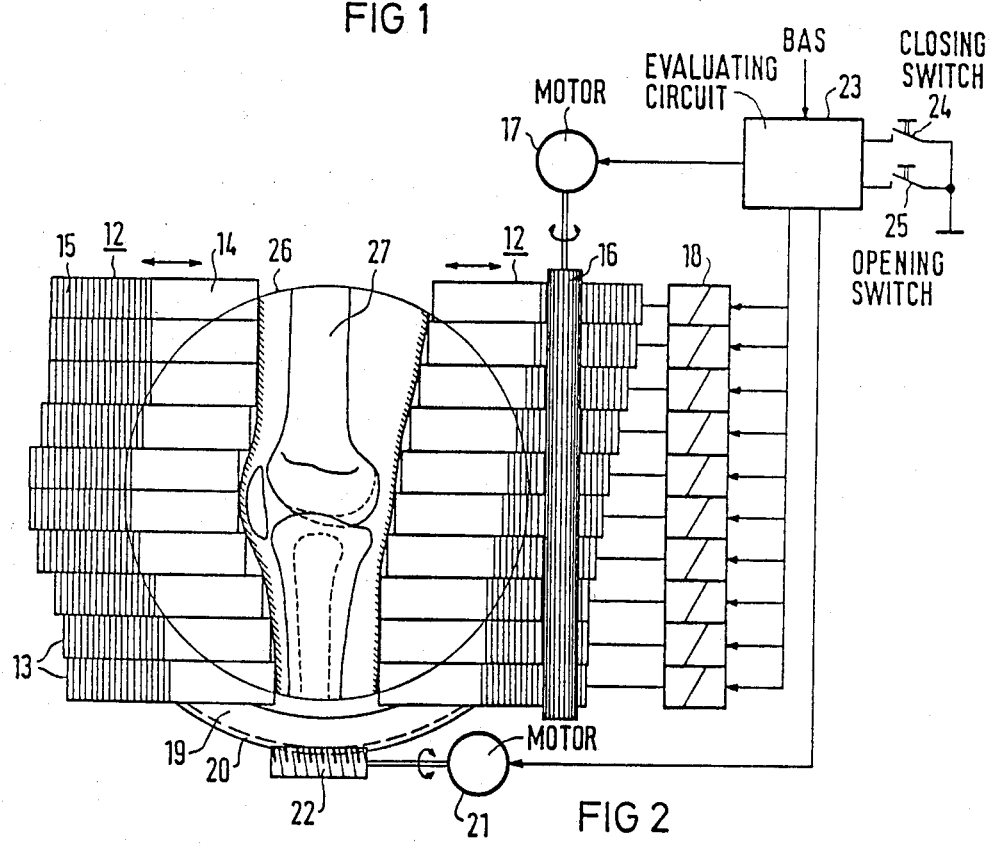
FIG. 2 shows schematically the construction of a diaphragm according to the invention.

In FIG. 2, the schematic construction of a semitransparent diaphragm 12 arranged in the primary ray shield 10 is represented. Diaphragm 12 consists of a plurality of strip-shaped blades 13 arranged parallel and side by side in two opposed groups. The blades 13 which have in their distal areas 14 an absorption value which corresponds to an iron plate of a thickness of 0.4 mm to 3.5 mm. In their rear areas the blades 13 are formed as a toothed rack 15, into which there engage toothed rollers 16 driven by motors 17 (only one shown). Each rack 15 of the blades 13 has associated with it a coupling magnet 18, which upon actuation of the racks 15 presses against the motor-driven toothed rollers 16 and establishes a disconnectable connection with them.

The mechanism is connected with a diaphragm ring 19, which has on its outer edge tooth segments 20. A worm gear 22 driven by a motor 21 engages the tooth segments 20, so that the entire diaphragm 12 can be rotated about its center. An evaluating circuit 23, to which the video signal BAS is supplied, controls the motors 17 and 21 and the coupling magnets 18. At the evaluating circuit 23 are additionally connected two key switches 24 and 25, which respectively bring about the automatic closing and opening of the diaphragm 12.

The circular field 26 indicates the area irradiated by x-rays and corresponds to the x-ray picture reproduced on the monitor (not shown) of the x-ray/television system. As one exemplary object 27 being examined, there has been shown a knee joint.

In its initial position the diaphragm 12 is opened all the way; all blades 13 are outside the field 26. At start of radioscopy, after actuation of switch 24, the coupling magnets 18 are actuated by the evaluating circuit 23, so that the racks 15 engage in the toothed roller 16. At the same time the motors 17 are actuated in such a way that the blades 13 move toward each other and the diaphragm 12 closes slowly. Dependent on the video signal BAS, the individual coupling magents 18 are actuated, as will be explained later, by the evaluating circuit 23 in such a way that they drop one after the other and thus the racks 15 of the individual blades 13 are no longer in engagement with the still rotating toothed roller 16 when the video signal BAS belonging to the respective blade 13 drops below a certain preselected brightness level. The control of motor 21 by the evaluating circuit 23 causes a rotation of the diaphragm ring 19, so that the slit of diaphragm 12 is aligned relative to the object 27 being examined. After completed radioscopy, the motors 17 and the coupling magnets 18 are actuated by operation of switch 25 via the evaluating circuit 23 in such a way that the diaphragm is again opened completely.

Figure 3:
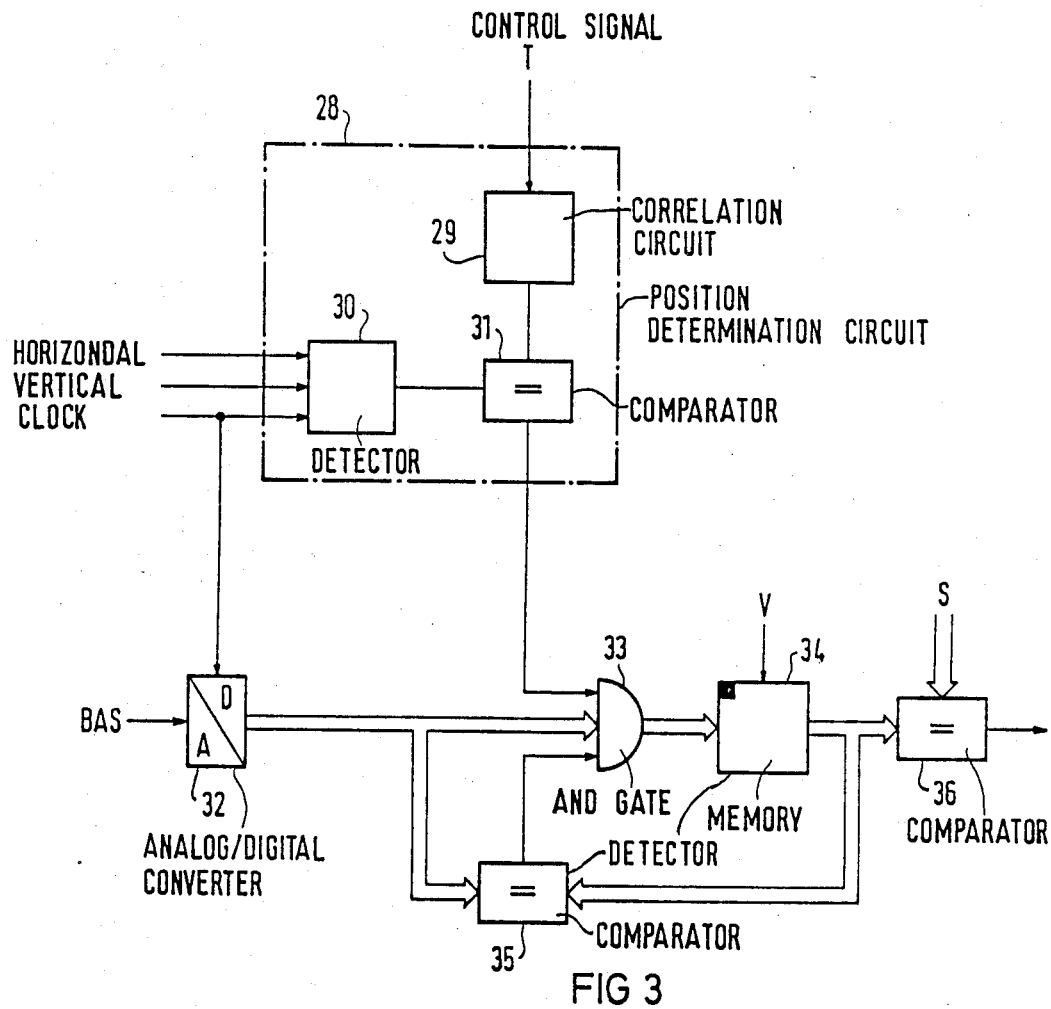
FIG. 3 is a block diagram of the evaluating logic circuit represented in FIG. 2.

In FIG. 3 is shown the evaluating circuit 23, which comprises a circuit 28 for position determination of the blades 13 within the video picture. It coordinates the effective video signal BAS with the individual blades 13. It contains a circuit 29 for determining the areas correlated with the individual blades 13, i.e. the area which each blade 13 can completely cover. The circuit 29 may be, for example, a memory in which these areas are contained. To this circuit 29 a control signal T is supplied which identifies the blade 13 just then selected. A detector 30 is also contained in circuit 28, to which the horizontal and vertical pulses H and V and the clock pulse B of the television chain are supplied, serves to determine the instantaneous position of the scanned video signal BAS. The output signals of circuit 29 and of detector 30 are supplied to a first comparator 31, which generates an output signal if the video signal BAS lies within the area of the blade 13 currently being actuated.

The video signals BAS coming from the television camera is supplied to an analog/digital converter A/D 32, which acts as an adaptation stage and to which the clock pulse is supplied for digitization. The digital output signal of the A/D converter 32 is supplied to an AND element 33 acting as gate circuit. The digital output values of the A/D converter 32 are transmitted by the AND element 33 only if the circuit 28 has determined that the arriving video signal BAS belongs to the blade 13 currently being actuated. The output of the AND element 33 is connected to a memory 34 whose output is placed on a second comparator 35, to the second input of which the effective video signal of the A/D converter 32 is supplied. The second comparator 35 generates an output signal if the new image element of the video signal BAS is greater than the old image element supplied by the memory 34, so that at the end of the scanning always the maximum amplitude value contained in the video signal area associated with the actuated blade 13 is present in memory 34. Thereby the memory 34, the second comparator 35, and the AND element 33 operates as a peak value detector. By the vertical pulses V the memory 34 is erased after each television picture, so that the maximum value can be determined anew.

The output of memory 34 is supplied to a third comparator 36, at the second input of which an adjustable threshold value S is present. The output signal of the third comparator 36 controls the selected copuling magnet 18 if the value stored in memory 34 exceeds the threshold value S.

In the following, the operation of the evaluating circuit 23 will be explained more specifically. To simplify matters, only one of the blades 13 will be considered. At start of radioscopy, a logically high, or H signal is supplied by circuit 28 as long as the image point supplied by the A/D converter 32 lies within the area in the television picture belonging to the actuated blade 13. Since at the start no value is as yet contained in memory 34, the second comparator 35 also supplies an H signal, so that the first image point is read into memory 34. This takes place within the area belonging to the actuated blade 13 until the maximum value of the image points is contained in memory 34 and the following image points are equal to or smaller than the stored image point, so that the second comparator 35 supplies a logically low, or L signal to the AND element 33, thus blocking it.

If the stored image point is brighter than the adjusted threshold value S, the third comparator 36 supplies an output signal, so that the coupling magnet 18 belonging to the actuated blade 13 is actuated and blade 13 is moved by motor 17, so that the diaphragm 12 closes in this area. By the vertical pulse V the memory 34 is erased, so that for the next television frame again the maximum value can be read into the memory. This takes place until blade 13 has approached the object 27 being examined, after which the maximum value of the image points decreases within the area of blade 13. If the maximum value falls below the threshold value S supplied to the comparator 36, the coupling magnet 18 of the actuated blade 13 is no longer excited, so that it drops and blade 13 remains in this half-closed position. Subsequently the other blades 13 are actuated in the same manner, so that they assume for example the position shown in FIG. 2.

Instead of the successive actuation of the coupling magnets 18 and of the blades 13, they may be actuated alternately in multiplex operation if at least one memory 34 and a third comparator stage 36 are provided for each of the blades 13. By a multiplex circuit then required, the output signal of the AND element 33 is supplied to the corresponding memory 34, and the output signal of this memory 34 to the second comparator and the respective third comparator. As a result there occurs an almost simultaneous displacement of the blades 13, so that the diaphragm 12 closes as far as is needed over its entire width within a very short time.

The threshold value S supplied to the third comparator 36 can, for example, be adjusted continuously by the person being examined. Alternatively, organs, for example, can be represented correspondingly if the threshold value is selectable via pushbuttons to correspond to the transmission characteristics of the organ under investigation.

Instead of the rack 15 and toothed roller 16, a rubber roller and a friction surface may being about the adjustment of the blades 13. The coupling magnets 18 may be replaced, for each side of the diaphragm 12, by a coupling magnet which is displaced mechanically and couples each blade 13 individually and successively with the rack 16.

The rotation of the diaphragm ring 19 and hence the orientation of the slit of diaphragm 12 may jointly be coupled with the television camera, so that the longitudinal direction of the blades always lies along the scanning direction of the television camera. Or it may be effected by a similar evaluation of the television image from the video signal BAS.

Those skilled in the art will understand that changes can be made in the preferred embodiments here described, and that these embodiments can be used for other purposes. Such changes and uses are within the scope of the invention, which is limited only by the claims which follow.

What is claimed is:

1. An x-ray apparatus, comprising in combination:
    an x-ray tube for transmission of x-rays through an object under examination;
    an image intensifier for receiving said x-rays transmitted through said object;
    a video camera coupled to said image intensifier for generating a video signal corresponding to the attenuation of said x-rays transmitted through said object;
    a semitransparent diaphragm arranged between said x-ray tube and said image intensifier, said diaphragm being positioned close to said x-ray tube and comprising
        a plurality of elongated blades which are arranged in two opposed groups which bound a region of interest, all the blades in each group being arranged side by side and abutting each other in a manner that each blade is slideable with respect to adjacent blades, and
        means for individually sliding said blades in amounts which depend upon the dimensions of said object within said region; and
    a circuit for evaluation coupled to said video camera for receiving said video signal and for generating a control signal therefrom for controlling said means for sliding said blades, said evaluation circuit comprising
        means for correlating areas of said region with the blades, which can cover and uncover said areas,
        means for monitoring said video signal for a component of interest, said component of interest being associated with a pixel within said region which is located at an end of a blade of interest which is sliding, and
        means for controlling the sliding of said sliding blade of interest in a manner that said object remains substantially uncovered by said blade.

2. The x-ray apparatus of claim 1, wherein said region has a centerline and said blades are perpendicular to said centerline.

3. The x-ray apparatus of claim 1, wherein said region has a centerline and said blades are at an angle of at least 20° and at most 90° with respect to said centerline.

4. The x-ray apparatus of claim 1, further comprising first and second motors each corresponding to one of the groups of blades, and means for engaging individual ones of the blades with its corresponding motor, such that said individual blades are made to slide independently.

5. The x-ray apparatus of claim 4, wherein said engaging means comprises a coupling magnet.

6. The x-ray apparatus of claim 1, further comprising a rotatable ring to which said blades are mounted, such that said blades may be aligned with the scanning direction of said video camera.

7. The x-ray apparatus of claim 1, wherein said evaluation circuit comprises:
    a position determination circuit for correlating the position of said blades with said video signal from clock signals and from control signals which determine selected blades of interest;
    a converter stage for receiving said video signal;
    a gate coupled to said position determination circuit and said converter stage, said gate providing an output signal;
    a detector receiving said output signal of said gate for detecting the peak value of said video signal, said detector issuing a detector output signal; and
    a comparator for comparing said detector output signal with an adjustable threshold, said comparator generating a control signal for controlling said means for sliding said blades.

* * * * *